United States Patent [19]

Tamm

[11] 4,371,262
[45] Feb. 1, 1983

[54] HOLDER FOR ABSORPTION SPECTROMETER ATOMIZING FURNACE CAPSULES

[75] Inventor: Rolf G. A. Tamm, Salem, Fed. Rep. of Germany

[73] Assignee: Bodenseewerk Perkin-Elmer & Co., GmbH, Uberlinge, Fed. Rep. of Germany

[21] Appl. No.: 918,628

[22] Filed: Jun. 23, 1978

[30] Foreign Application Priority Data

Jul. 7, 1977 [DE] Fed. Rep. of Germany ....... 2730614

[51] Int. Cl.² ............................................... G01J 3/30
[52] U.S. Cl. ...................................... 356/312; 356/315
[58] Field of Search ........................ 356/312, 315, 244

[56] References Cited

FOREIGN PATENT DOCUMENTS 2501507  7/1976  Fed. Rep. of Germany ...... 356/312

OTHER PUBLICATIONS

"Universal Mounting for Electrically Heated Atomic-Absorption Analyzers"; L'Vov et al.; Russian Journal of Applied Spectroscopy; Feb. 1976; vol. 24, #2, pp. 372-373.

Primary Examiner—Vincent P. McGraw

[57] ABSTRACT

Graphite capsules are supported in a flame in an atomic furnace between electrical current heating electrodes that are mounted in the faces of a pair of water-cooled housings, one of which may be pivoted by a pneumatic piston to facilitate removal and insertion of the capsules and which provides a constant and firm contact pressure against the capsule ends independently of capsule length or diameter variations.

7 Claims, 4 Drawing Figures

HOLDER FOR ABSORPTION SPECTROMETER ATOMIZING FURNACE CAPSULES

CROSS-REFERENCE TO RELATED APPLICATIONS

The apparatus described and claimed herein is related to pending United States Patent Application Ser. No. 790,730, filed Mar. 27, 1978.

BRIEF SUMMARY OF THE INVENTION

In analyses by atomic absorption spectrometers, the sample to be analyzed is heated to a temperature at which the element of interest in the sample becomes atomized. The cloud of atoms is then penetrated by a light beam that is generated by the spectrometer equipment to contain the characteristic resonant lines of the element to be measured, and the measurements of the energizing beam provides an indication of the absorption of the beam by the atom cloud and hence the degree of concentration of that element.

There are several methods for heating a substance to release the contained elements of interest. Liquids are generally heated in graphite tubes coaxially aligned with the measuring light beam and heated by an electrical current passing between the tube ends. Solid sample materials are effectively heated by the so-called "capsule-in-flame" method in which the sample is inserted into a cavity of a graphite capsule which is then sealed and electrically heated to the required atomizing temperature while engulfed in a cool gas flame of low oxygen content. The atomized elements heated by the electrical heating current then diffuse through the graphite and the flame from the burner, which also serves as a protective inert gas atomosphere for the heated capsule, transports the atomized sample components into the path of the measuring beam while providing sufficient heat to maintain the samples in their atomized state.

A device which performs the above discussed capsule-in-flame process is described in an article by B. V. L'Vov et al. entitled "A Universal Mounting for Electrically Heating Atomic-Absorption Analyzers", published in the Russian *Journal of Applied Spectroscopy*, (February 1976) at Volume 24, No. 2, Pages 372–374. In this article, L'Voy shows and describes a device having two water-cooled housings spaced apart on a base plate and having coaxial apertures for the passage of the spectrometer measuring beam. One of the water-cooled housings is dovetailed for linear movement parallel to the axis and is spring-biased toward the second housing. The graphite capsule is positioned between the two housing portions below the measuring beam aperture and the biasing spring provides the required contact pressure against the ends of the capsule. The two housings are connected to a current supply so that heating current may pass through to heat the capsule. A gas burner is located on a support on the base member below the capsule to provide the required flame that both transfers the diffused atoms into the path of the measuring beam and also prevents oxygen from reaching the exterior surface of the graphite capsule, thereby preventing combustion of the capsule itself.

While the device described in the above referenced article performs quite satisfactorily for laboratory purposes, it suffers from certain drawbacks that render it impractical. For example, in all furnaces employing the capsule-in-flame method, it is necessary to change the capsule after each analysis. First, the burner has to be extinguished or removed from the area of the capsule. The movable housing portion then must be retracted manually against the action of the spring and the capsule has to be removed and replaced by a new capsule containing another sample for analysis. Different capsules may have different lengths and/or diameters and all generally have a certain degree of expansion when heated. This naturally varies the contact pressure of the electrodes against the capsule ends. Since the graphite capsules are very delicate, variations in contact pressures against the capsule ends presents considerable problems in practice. If the contact pressure exceeds a certain level, the capsule will readily fracture, thereby destroying the test and possibly a rare and valuable sample. Insufficient contact pressure may result in arcing between an electrode and its capsule end and a high heat concentration at the end instead of in the area of the contained sample. It is, therefore, essential that proper contact pressure between the electrodes and the ends of the capsule must be maintained to provide adequate even heating without danger of fracturing the graphite capsule.

The invention described herein is for a capsule holder which facilitates the mounting and removal of the capsule and, in addition, ensures an accurate and constant contact pressure between the capsule and the electrodes.

Briefly described, the invention includes a base that supports two water-cooled housings having coaxial apertures for the passage of the absorption spectrometer measuring beam, and having facing electrode elements below these apertures. One housing is mounted to the base by a pivot which permits the housing to be swung down and away from the facing housing. This pivotable housing is actuated by a pneumatic piston, the cylinder of which is mounted to the opposite stationary housing. The housings are thus separated by gas pressure for removal and insertion of capsules and a carefully regulated gas pressure maintains constant contact pressure between the electrodes and the capsule ends independently of size variations in the capsules. The burner is conveniently supported on the pneumatic piston and is easily rotated out of position, without need to extinguish the flame, during capsule changes.

DESCRIPTION OF THE DRAWINGS

In the drawings which illustrate a preferred embodiment of the invention.

DETAILED DESCRIPTION OF THE PREFERRED EMBODIMENT

Figure 1:
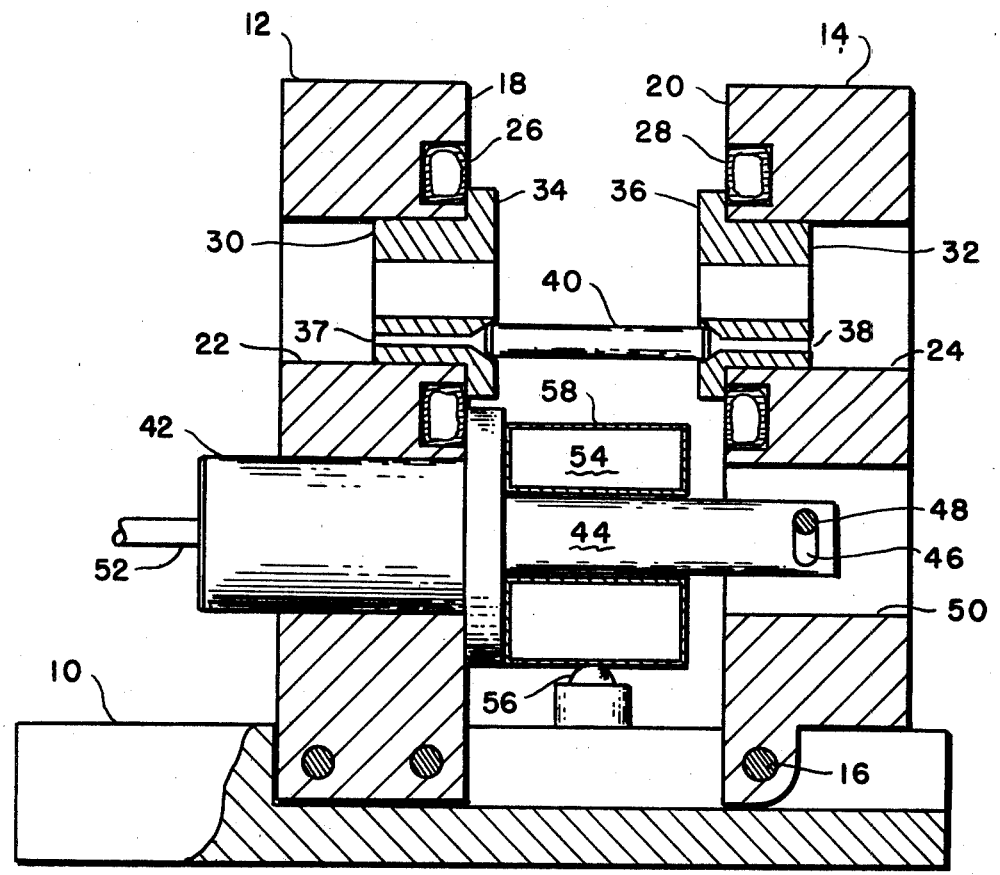
FIG. 1 is a sectional elevation view illustrating a graphite capsule supported between electrodes.

In the elevation view of FIG. 1, a base 10 adapted to be adjustably coupled to associated atomic absorption spectrometer apparatus rigidly supports a vertical stationary housing 12 and a second movable housing 14 which is coupled to the base 10 by a pivot 16. The housings 12 and 14 are block-shaped and spaced from each other by a suitable spacing dictated by the length of a typical graphite capsule. The housings 12 and 14 have two substantially parallel facing surfaces 18 and 20, respectively, and the housings 12 and 14 are provided with coaxial apertures 22 and 24, respectively, the axes of which are perpendicular to the facing surfaces 18 and 20. Water cooling jackets 26 and 28 are cut into the facing surfaces 18 and 20, respectively, in an annular path around the apertures 22 and 24, respectively.

Inserted into apertures 22 and 24 are cylindrical electrodes 30 and 32, respectively, each having a central aperture coaxial with the apertures 22 and 24 and each having a flange 34 and 36, respectively, that engages the surfaces 18 and 20. Mounted below the central apertures of the electrodes 30 and 32 are holes 37 and 38, respectively. Holes 37 and 38 are coaxial with each other and on an axis parallel with apertures 22 and 24. As shown, holes 37 and 38 have conical counterbores at their facing ends to assure the centering of a graphite capsule 40 and also to provide a maximum conductive surface between the electrodes and the ends of the capsule 40. A high heating current can be passed through the capsule 40 via the electrodes 30 and 32 which are respectively coupled to a current supply source in a conventional manner (not shown).

Housing 14 can be rotated about the pivot axis 16 by a pneumatic servomotor system which includes a pneumatic cylinder 42, firmly supported in an aperture of the housing 12, which contains a piston that drives the piston rod 44. The distal end of rod 44 contains a vertical slot 46 that loosely engages a pin 48 which is rigidly connected to the housing 14 and bridges its aperture 50. Actuation of the piston rod 44 is under the control of pressurized air or other gas admitted and withdrawn into the cylinder 42 through the tubing 52.

A gas burner 54, to be subsequently described in detail in connection with FIG. 4, loosely engages the piston rod 44 and is maintained in position by a spring-loaded detent ball 56 engaging an indentation in the burner housing. As illustrated in FIG. 1, the burner 54 is positioned directly below the graphite capsule 40 and, as will be subsequently described, contains a flat top surface 58 perforated with a plurality of gas outlet openings to provide an oxygen-weak flame to surround the capsule 40. Because the burner 54 is loosely fitted to the piston rod 44 and maintained by the spring-loaded ball 56, the flat burner surface 58 is easily rotated on the rod 44 and away from the capsule whenever a capsule change is to be made. If desired, the tubular core of the burner assembly may have a spiral groove engaging a key pin in the rod 44 so that movement of the rod will automatically rotate the burner.

Figure 2:
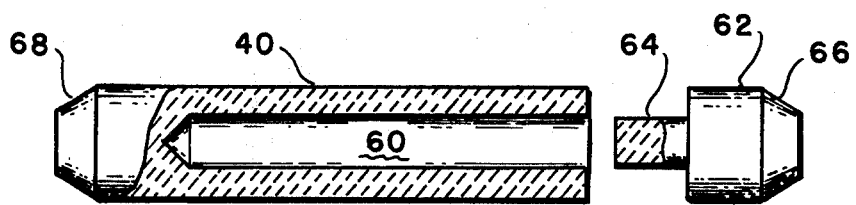
FIG. 2 is a sectional elevation view illustrating a typical graphite capsule used with the structure of FIG. 1.

FIG. 2 is a sectional view of a typical graphite capsule, such as the capsule 40 of FIG. 1. Capsule 40 is formed from a small graphite rod having a longitudinal blind bore 60 and is provided with a plug 62 having a core member 64 configured to fit within the bore 60. The exterior end of the plug 62, as well as the opposite end of the capsule 40, are provided with conical contact surfaces 66 and 68, respectively. Conical surfaces 66 and 68 are adapted to mate with the countersunk sections of holes 37 and 38 in the electrodes 30 and 32, respectively, of FIG. 1, to provide automatic centering of the capsule within the electrodes and a maximum electrical conductive area between the electrodes and the capsule. Electrical heating current applied through the capsule ends pass through a smaller cross-section, and have a higher resistance, in the center portion of the capsule. The center is therefore heated more rapidly and to a higher temperature to atomize the element of interest in the sample.

Figure 3:
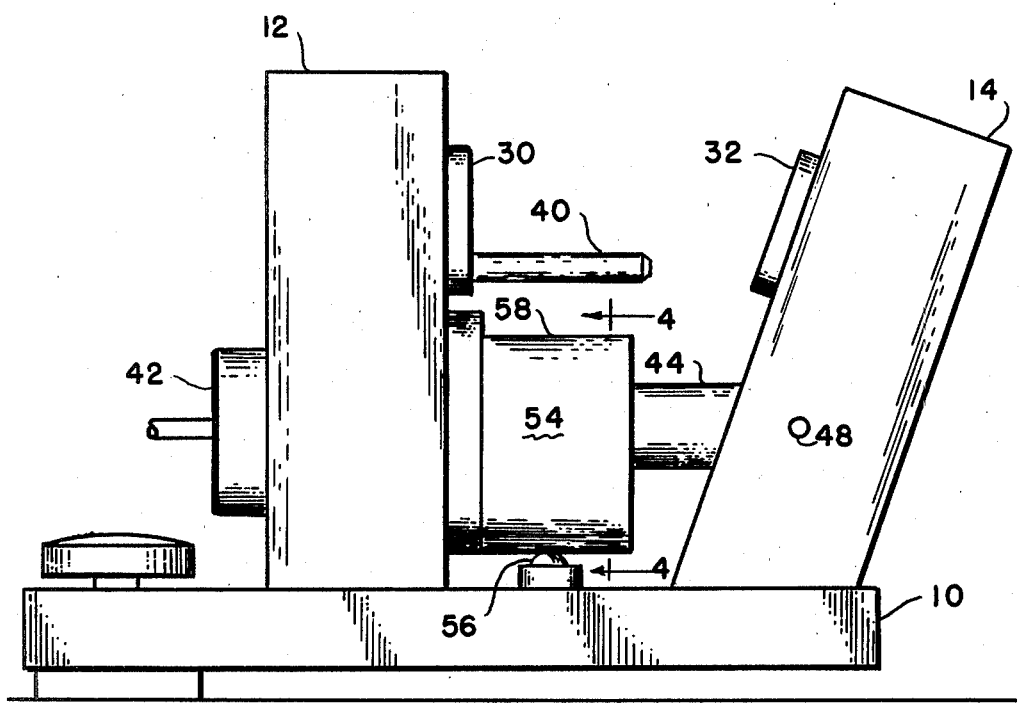
FIG. 3 is an elevation view of the structure of FIG. 1 in an opened position.

FIG. 3 is an elevation view showing the apparatus of FIG. 1 with the housing 14 pivoted to permit removal and insertion of the graphite capsule 40. It will be noted that burner 54 is still positioned with its flat burner surface 58 facing the capsule 40. Unless the burner 54 is automatically rotated, as previously described, the burner 54 maintains its position as the piston rod 44 is extended, as shown, because the spring-loaded detent ball 56 engages a mating indentation in the bottom surface of the burner 54.

Figure 4:
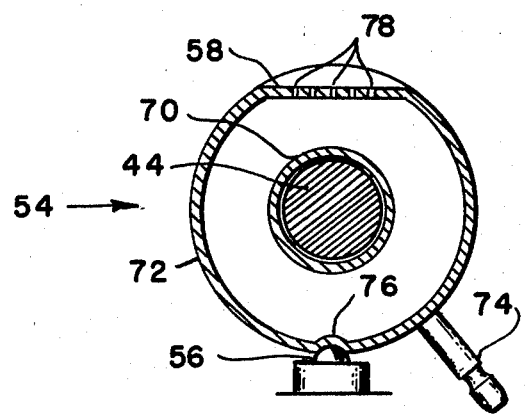
FIG. 4 is a sectional elevation view of the burner taken along the lines 4—4 of FIG. 3.

FIG. 4 is a sectional view of the burner 54 taken along the lines 4—4 of FIG. 3. The burner 54 includes a central tubular section 70 having an inside diameter slightly larger than the diameter of the piston shaft 44. Burner 54 also has an exterior tubular section 72 and both interior section 70 and exterior section 72 are sealed at the ends by disc members to provide a sealed enclosure through which the piston rod 44 may easily move. Exterior section is provided with a gas inlet tube 74 that enters the burner 54 near its bottom, as shown. At the bottom of the burner 54, the spring-loaded detent ball 56 engages an indentation 76 in the bottom of the exterior section 72. The top of the exterior section opposite the indentation 76 is a flat surface 58, as previously explained. Flat surface 58 contains a plurality of gas outlet apertures 78.

OPERATION

In its initial state, the pneumatic cylinder is actuated so that piston rod 44 is extended to rotate the housing 14 about the pivot 16 as shown in FIG. 1. The burner 58 is rotated on the shaft 44 so that the flame is no longer directed against the capsule 40. It is now possible to remove the capsule 40 by gently tapping it out with a small drive pin inserted through the apertures 37 or 38. The new capsule is filled with sample to be analyzed and is held in position between the countersunk apertures in the electrodes 30 and 32 as the pneumatic cylinder 42 draws in the piston rod 44 and the housing 14. The countersunk holes 37 and 38 in the electrodes 30 and 32 align the graphite capsule 40 which is supported firmly between the electrodes 30 and 32. Contact pressure is determined by the pressure of the fluid acting within the pneumatic cylinder 42 and this pressure is independent of variations in length of the capsule 40 or of different capsules. Burner 54 is then rotated back on the shaft into its operating position as illustrated in FIG. 4 to engulf the capsule 40 with the gas flame. Heating current is then passed through the capsule 40 via the electrodes 30 and 32 and the capsule is heated to a predetermined temperature at which the elements of interest are atomized. These components diffuse through the porous walls of the graphite capsule 40 while less volatile components remain unatomized and are retained in the capsule. The atomic components diffusing through the walls of the capsule 40 are carried upward by the flame, which also acts to prevent oxygen from the capsule surface to prevent combustion of the capsule. The atoms are transported into the spectrometer measuring beam passing through the coaxial apertures of the housings 12 and 14 and their electrodes 30 and 32, respectively.

Having thus described the invention, what is claimed is:

1. An absorption spectrometer atomizing furnace structure for supporting a closed graphite sample capsule in a flame and between first and second electrical heating current electrodes respectively mounted in fluid-cooled first and second housings having coaxial apertures above and adjacent said sample capsule for the passage of a spectrometer measuring beam, said structure comprising:
- a base member;
- means for rigidly connecting the first fluid-cooled housing to said base member;
- pivot means coupling the second housing to said base member in spaced and facing relationship with said first housing, said pivot means permitting said second housing to swing away from said first housing to facilitate removal and insertion of the graphite sample capsule;
- said second housing being pivoted by a pneumatic actuator including a pneumatic cylinder coupled to said first housing and operating a piston rod the distal end which engages a pivot pin coupled to said second housing; and
- a burner assembly loosely coupled to said piston rod, said burner assembly comprising an annular chamber having a flat exterior surface section containing a plurality of gas outlets.

2. The structure claimed in claim 1 wherein said burner is rotatable on said piston rod and held in operating position by a spring-biased detent ball assembly coupled to said base and engaging an indentation in the bottom surface of said annular burner.

3. The structure claimed in claim 1 wherein the first and second electrodes are supported in facing relationship in the coaxial apertures of said first and second housings, each of said electrodes having a central aperture coaxial with the housing apertures for the passage of the spectrometer measuring beam.

4. The structure claimed in claim 3 wherein said sample capsule is formed from a graphite rod having a blind longitudinal bore, said capsule including a cylindrical plug having an enlarged exterior end section, the exterior end section of said plug and the opposite end section of said rod being provided with conical contact surfaces.

5. The structure claimed in claim 4 wherein each of said first and second electrodes have a second aperture parallel with said central aperture and displaced therefrom, said second aperture having a conical counterbore adapted to mate with the conical end of said sample capsule.

6. An absorption spectrometer atomizing furnace structure for supporting a closed graphite sample capsule in a flame comprising:
- first and second housings having coaxial apertures above and adjacent the sample capsule for the passage of a spectrometer-measuring beam,
- first and second electrical heating current electrodes respectively carried by said first and second housings,
- a base member;
- means for rigidly connecting said first housing to said base member;
- pivot means coupling said second housing to said base member in spaced and facing relationship with said first housing for enabling said second housing to swing away from said first housing to facilitate removal and insertion of the graphite sample capsule;
- said second housing being pivoted by an actuator including a fluid-actuated cylinder coupled to said first housing, a piston rod carried by said cylinder, and a pivot pin coupled to said second housing, said rod engaging said pivot pin; and
- a burner assembly carried by said actuator, said burner assembly comprising a chamber having an exterior surface section containing a plurality of gas outlets underlying the sample capsule when said second housing lies in spaced facing relationship with said first housing with the sample capsule therebetween.

7. The structure according to claim 6 wherein said burner assembly is movable about said piston rod between a first operating position with said gas outlets underlying the sample capsule when the second housing lies in spaced facing relationship with said first housing with the sample capsule therebetween and a second position laterally offset to one side of said housing when said second housing is swung away from said first housing and the sample capsule is removed from between said housings.

* * * * *